(12) United States Patent
Hansen

(10) Patent No.: US 8,411,272 B2
(45) Date of Patent: Apr. 2, 2013

(54) METHOD AND APPARATUS FOR THE ANALYSIS OF MATERIALS

(75) Inventor: Anthony D. A. Hansen, Berkeley, CA (US)

(73) Assignee: Magee Scientific Corporation, Berkeley, CA (US)

( * ) Notice: Subject to any disclaimer, the term of this patent is extended or adjusted under 35 U.S.C. 154(b) by 571 days.

(21) Appl. No.: 12/534,343

(22) Filed: Aug. 3, 2009

(65) Prior Publication Data

US 2010/0027013 A1 Feb. 4, 2010

Related U.S. Application Data

(60) Provisional application No. 61/085,957, filed on Aug. 4, 2008.

(51) Int. Cl.
*G01N 21/00* (2006.01)
*G01N 1/00* (2006.01)

(52) U.S. Cl. .......................................... 356/432; 356/38

(58) Field of Classification Search ........................ None
See application file for complete search history.

(56) References Cited

U.S. PATENT DOCUMENTS

| | | | | |
|---|---|---|---|---|
| 3,204,449 A | * | 9/1965 | Fordyce | 73/38 |
| 3,419,879 A | * | 12/1968 | Pelavin | 346/33 R |
| 3,489,525 A | * | 1/1970 | Natelson | 422/64 |
| 3,526,480 A | * | 9/1970 | Reid et al. | 422/66 |
| 3,653,773 A | * | 4/1972 | Childs | 356/432 |
| 3,654,801 A | * | 4/1972 | Keefer et al. | 73/28.04 |
| 3,690,833 A | * | 9/1972 | Ferrari | 436/53 |
| 3,769,505 A | * | 10/1973 | Lee et al. | 250/394 |
| 3,770,356 A | * | 11/1973 | Kimura | 356/434 |
| 3,837,808 A | * | 9/1974 | Sugimoto et al. | 436/136 |
| 3,975,727 A | * | 8/1976 | Mader et al. | 341/140 |
| 4,123,159 A | * | 10/1978 | Hollander et al. | 356/38 |
| 4,395,493 A | * | 7/1983 | Zahniser et al. | 435/286.4 |

(Continued)

FOREIGN PATENT DOCUMENTS

JP 2001343319 A * 12/2001

OTHER PUBLICATIONS

Petzold, Andreas et al., 'Method Comparison Study on Soot-Selective Techniques,' 1995, Mikrochimica Acta 117, pp. 215-237.*

(Continued)

*Primary Examiner* — Gordon Stock, Jr.
(74) *Attorney, Agent, or Firm* — Steven R. Vosen

(57) ABSTRACT

An apparatus and method are presented for the analysis of materials. The apparatus includes two or more similar analyzers, with the output of the analyzers combined to provide improved measurements. The apparatus may be, for example, a differential photometric analyzer, such as the AETHALOMETER®. The apparatus and method includes providing flows to the analyzers such that the rate of accumulation per filter area differs for the two or more analyzers. The output of the apparatus or method may be a concentration, such as the concentration of black carbon particulates. Additionally, the output may be an optical measure of particulates that is useful for characterizing the source or history of the particulates.

33 Claims, 3 Drawing Sheets

U.S. PATENT DOCUMENTS

| | | | | |
|---|---|---|---|---|
| 4,893,934 | A | 1/1990 | Hansen | |
| 6,406,633 | B1 * | 6/2002 | Fischer et al. | 210/659 |
| 7,038,765 | B2 | 5/2006 | Petzold et al. | |
| 8,299,449 | B2 * | 10/2012 | Febo | 250/573 |
| 2004/0156036 | A1 * | 8/2004 | Petzold et al. | 356/38 |
| 2005/0041774 | A1 * | 2/2005 | Saitoh et al. | 378/53 |
| 2008/0100826 | A1 * | 5/2008 | Sharpe | 356/51 |
| 2009/0081804 | A1 * | 3/2009 | Tuchman | 436/158 |
| 2010/0265508 | A1 * | 10/2010 | Schumann et al. | 356/438 |
| 2012/0229798 | A1 * | 9/2012 | Mocnik et al. | 356/51 |

OTHER PUBLICATIONS

Hanel, Gottfried, 'Radiation Budget of the Boundary Layer. Part II: Simultaneous Measurement of Mean Solar Volume Absorption and Extinction Coefficients of Particles,' 1987, Beitr. Phys. Atmosph. vol. 60, No. 2.*

Batelle; Environmental Technology Verification Report, "Magee Scientific Aethalometer Particulate Carbon Monitor"; Aug. 2001.

* cited by examiner

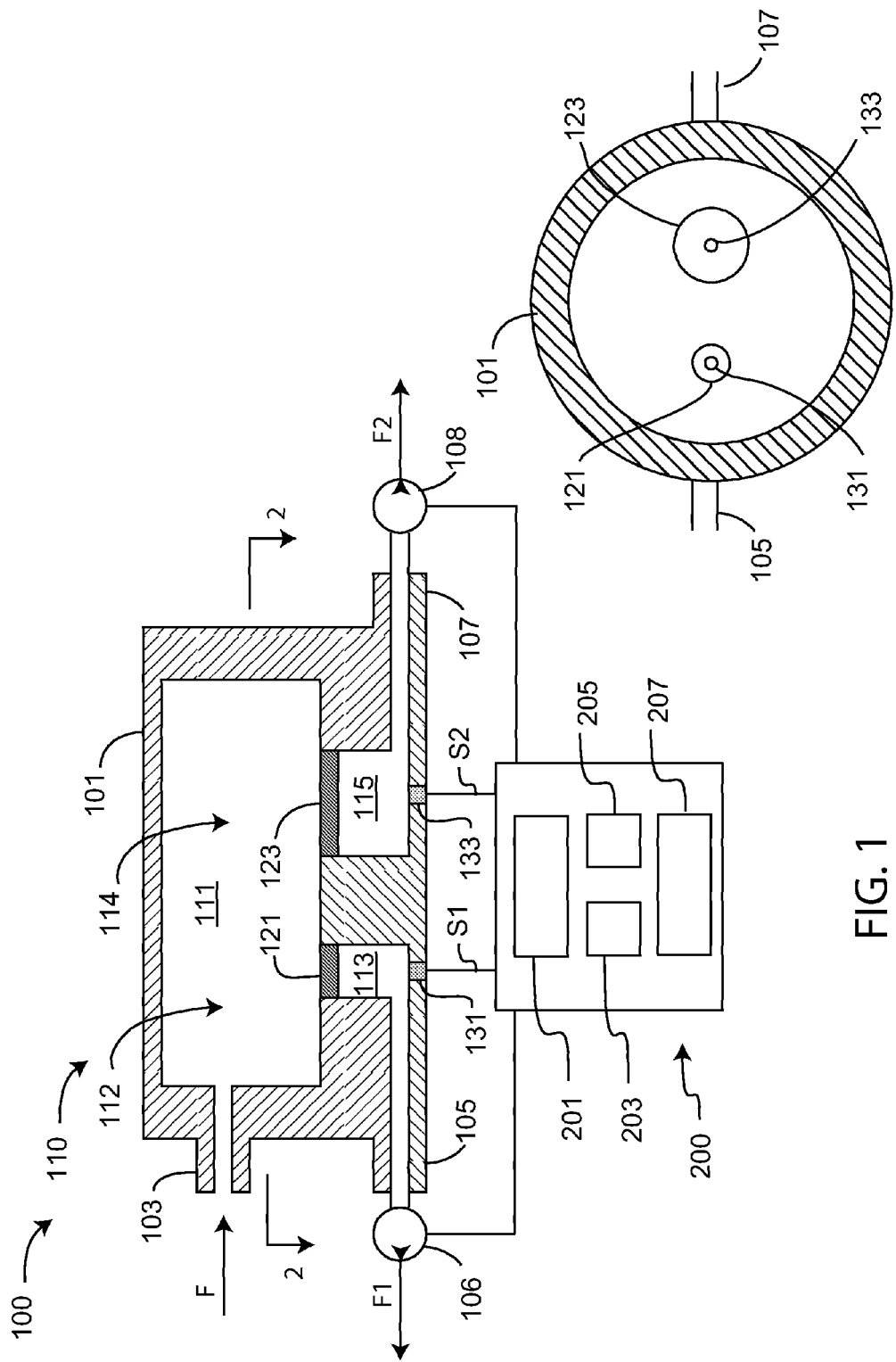

US 8,411,272 B2

METHOD AND APPARATUS FOR THE ANALYSIS OF MATERIALS

CROSS-REFERENCE TO RELATED APPLICATIONS

This application claims the benefit of U.S. Provisional Application No. 61/085,957, filed Aug. 4, 2008, the entire contents of which are incorporated herein by reference and made part of this specification.

BACKGROUND OF THE INVENTION

1. Field of the Invention

The present invention generally relates to a method and apparatus for analysis, and more specifically to a method and apparatus to improve the analysis of chemical, physical or biological materials.

2. Discussion of the Background

Most instruments for characterizing a material of interest rely on indirect measurements of a property of interest. Typically, there is an assumed functional relationship between a measured quantity and a property of interest. Thus, for example, there is a linear relationship between the mass and the weight of an object. Accordingly, a simple calibration of a scale allows the mass of an object to be inferred from a measure of the object's weight.

Some instruments have more complex responses. Thus, for example, the electric potential of a thermocouple is a non-linear function of the thermocouple temperature. Since thermocouples are well characterized, a polynomial function may be used to convert the thermocouple output into a temperature. Thus measurements performed by techniques that are well-understood or well-characterized, may be used to a high degree of accuracy.

However, some instruments may have responses that are not understood well enough to generally correct for errors in the instrument response. Thus, for example, if certain effects alter the output of an instrument and are not taken into account, then the use of the measurement may produce errors. There exists a need for a method and apparatus to provide for improved accuracy of measurements having complex responses.

BRIEF SUMMARY OF THE INVENTION

The present invention is an apparatus and method that corrects for certain instrument errors in the measurements of analytical instruments.

Certain embodiments provide an apparatus to measure constituents of interest in a sample. The apparatus includes a first analyzer, a second analyzer and a computer. The first analyzer includes a first filter having a first area to accumulate constituents of interest in a first portion of the sample having a first flow rate, and a detector to measure a property of accumulated constituents of interest on the first filter. The second analyzer includes a second filter having a second area to accumulate constituents of interest in a second portion of the sample having a second flow rate, and a detector to measure a property of accumulated constituents of interest on the second filter. The computer accepts the first detector and second detector measurements and provides an indication of the constituents of interest in the sample. In one embodiment, the indication is an estimate of the concentration of constituents of interest in the sample. In another embodiment, the indication is an indication of the nonlinearity of the response of one or more of the first analyzer and the second analyzer to an estimate of the concentration of constituents of interest in the sample.

Certain other embodiments provide an apparatus to measure constituents of interest in a sample having two or more sample portions. The apparatus includes two or more analyzers each including a filter to accumulate constituents of interest in a portion of the sample, and a detector to measure a property of accumulated constituents of interest. The apparatus further includes a computer to accept the detector measurements and provide an indication of the constituents of interest in the sample.

Certain embodiments provide a method for measuring a constituent of interest in a sample having a plurality of samples. The method includes accepting the output from a plurality of analyzers each adapted to measure the constituent of interest from a corresponding portion of the sample; and utilizing the output from the plurality of analyzers to provide an indication of the constituents of interest in the sample.

In certain embodiments, an apparatus includes a differential photometric analyzer. In certain other embodiments the differential photometric analyzers is an AETHALOMETER®.

These features together with the various ancillary provisions and features which will become apparent to those skilled in the art from the following detailed description, are attained by the apparatus and method of the present invention, preferred embodiments thereof being shown with reference to the accompanying drawings, by way of example only, wherein:

BRIEF DESCRIPTION OF THE SEVERAL VIEWS OF THE DRAWING

FIG. 1 a schematic of a first embodiment of a system;
FIG. 2 is a sectional view 2-2 of FIG. 1.

Figures 3, 4:
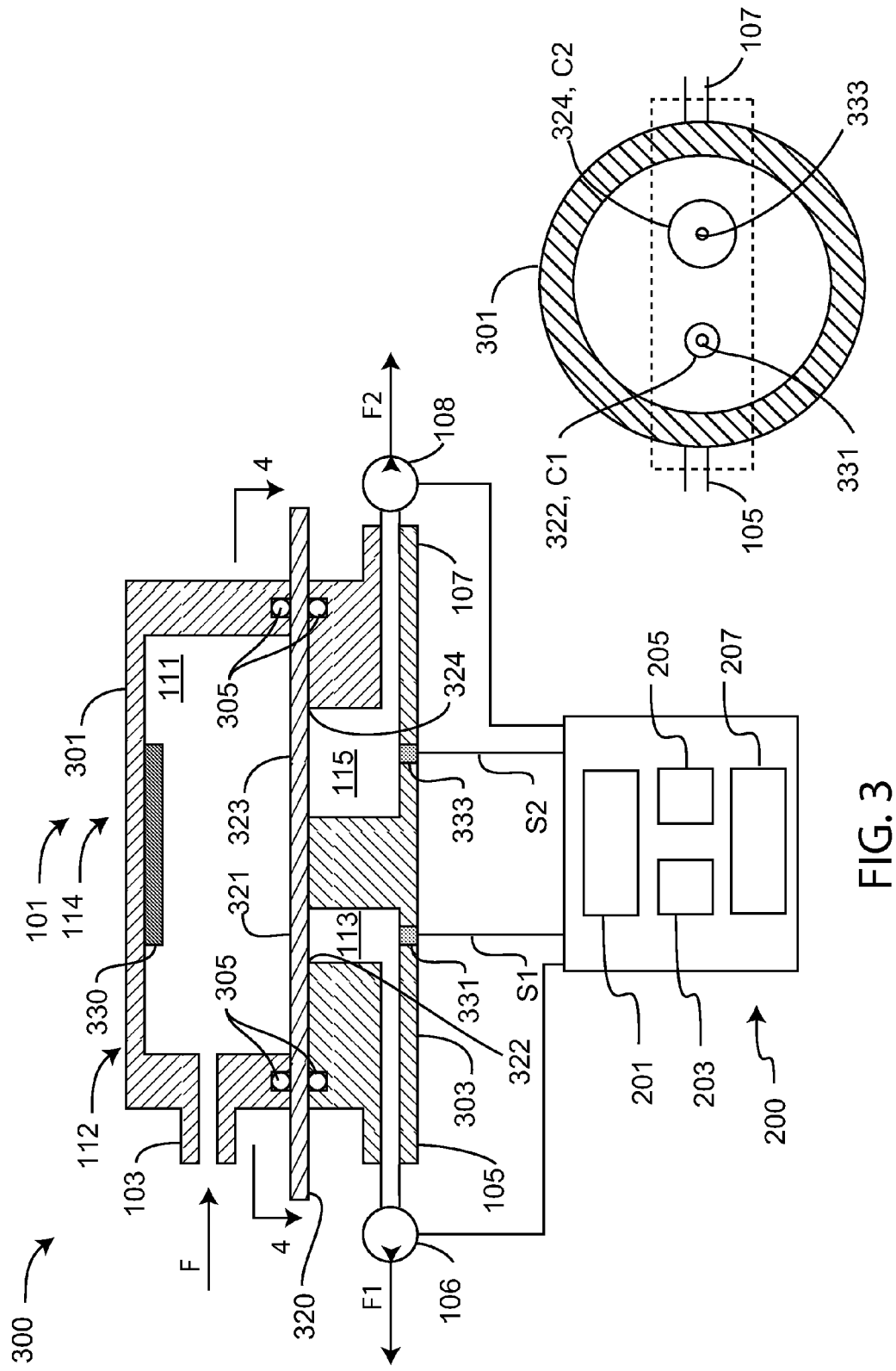
FIG. 3 a schematic of a second embodiment a system.
FIG. 4 is a sectional view 4-4 of FIG. 3.

Reference symbols are used in the Figures to indicate certain components, aspects or features shown therein, with reference symbols common to more than one Figure indicating like components, aspects or features shown therein.

DETAILED DESCRIPTION OF THE INVENTION

Various embodiments described herein are directed to analytic devices, systems, and methods that permit the identification, characterization, or quantification of one or more constituents of interest, such as an analyte, a biological component, or particulates. In particular, devices, systems, and methods are discussed that advantageously combine the output from multiple measurements of a sample, such as a flow of a gas containing a constituent of interest.

FIG. 1 is a schematic of the cross-section of one embodiment of a system 100 and FIG. 2 is a sectional view 2-2 of the embodiment of FIG. 1. System 100 includes an instrument 110 which may be in communication with a computer 200.

In general, instrument 110 is configured to accept a sample and perform measurements on two or more portions of the sample, which may be two portions of the flow of a sample. Instrument 110 thus may include one or more analyzers, each configured to measure a constituent of interest in each portion of the sample. In one embodiment, each measurement is essentially the same type of analysis, and the results of the separate analysis are combined and/or analyzed in computer 200 to provide an indication of the constituent of interest. As described subsequently, measurements from different portions of a sample may used, for example and without limitation, to obtain the improved accuracy over any one of the measurements, or to determine sample-dependent errors of an individual instrument calibration.

In one embodiment, instrument 110 may include a housing 101 having an inlet 103, a first outlet 105 having an associated first pump 106 and a second outlet 107 having an associated second pump 108. Housing 101 defines an interior that includes a volume 111 in fluid communication with inlet 103, a volume 113 in fluid communication with first outlet 105, and a volume 115 in fluid communication with outlet 107.

In one embodiment, first pump 106 may operatively draw flow from the apparatus through first outlet 105 at a flow rate F1, and a second pump 108 may operatively draw flow from the apparatus through second outlet 107 at a flow rate F2. Fluid thus enters inlet 103 with a flow rate F=F1+F2, and is divided into two streams within instrument 110. Alternatively, a single pump may be connected to both outlets 105 and 107, and valves may be provided to alter flow rates F1 and F2. System 100 may also include flow meters and/or mass flow controllers to measure or control one or more of flows F, F1, or F2. System 100 may thus separate flow F into flows F1 and F2 by providing volumes 111, 113, and 115 for the inlet fluid.

Instrument 110 includes multiple analyzers, shown for example and without limitation in FIG. 1 as a first analyzer 112 and a second analyzer 114. Instrument 110 may thus accept a sample and provide portions to each analyzer, shown for example and without limitation as a portion F1 provided to first analyzer 112, and as second portion provided to second analyzer 114. Analyzers 112 and 114 are configured to perform measurements on the samples within volumes 113 and 115, respectively and produce an output S1 and S1, respectively. Thus, for example, analyzer 112 includes a sensor 131 that performs a measurement on the sample within volume 113 and analyzer 114 includes a sensor 133 that performs a measurement on the sample within volume 115. Sensors 131 and 133 may be, for example, a combination of light source and detector that measure light absorption within volumes 113 and 115, respectively.

In another embodiment, analyzers 112 and 114 each perform a measurement on constituents of interest that are accumulated on a filter material, which may be a porous material through with the sample passes. Thus, for example, analyzer 113 may include a filter 121 and sensor 131 associated with volume 113, where sensor 131 is adapted to perform a measurement on constituents of interest that have accumulated on filter 131, and analyzer 114 may include a filter 123 and sensor 133 associated with volume 115, where filter 123 is adapted to perform a measurement one constitutions of interest that may have accumulated on filters 123. In one embodiment filters 121 and 123 are positioned and adapted to filter particulates of sample portions F1 and F2 that flow through volumes 113 and 115, respectively. Sensors 131 and 133 may be a combination of light source and detector that measure light absorption within filters 121 and 123.

A computer 200 includes a processor 201 and a memory 203. Memory 203 includes programming to control the operation of system 100 and to process the outputs S1 and S2. Memory 203 may also store, for example and without limitation, previous sensor outputs, including but not limited to background readings (without a filter, or with a fresh filter having no deposits), the results of previous measurements, and programming to permit computer 200 to execute mathematical algorithms to convert the sensor output into some indication of one or more constituents of interest.

Computer 200 may also include display 207 to present an indication of a constituent of interest, which may be for example and without limitation, a concentration of a constituent of interest or a direct or indirect measurement related to the constituent of interest. Computer 200 may further include communications interface 205 which may be used to transmit an indication of a constituent of interest to another computer or system, either wirelessly or over a wired network. Computer 200 may also accept provide signals to control pumps 106 and 108 and/or to accept input from flow controllers that may be associated with the pumps.

In certain embodiments, system 100 is an analytical instrument that performs measurements on particulates deposited on filters 121 and 123. In certain embodiments, sensors 131 and 133 produce readings that are proportional to the amount of particulates deposited on filters 121 and 123, respectively. Thus, for example, sensors 131 or 133 may be calibrated to provide an estimate of fluid concentration of particulates based on light absorption through filters 121 and 123. In some instances, the calibration is linear with the logarithm of light absorption, for example. It is known that for some measurements such as optical transmission through a filter with carbon black deposits, calibrations hold for low amount of particulate loading, and that the instruments produce errors in particulate concentration as that depends on the type of particulates and their density on the filter.

Examples of sensors 131 and 133 include, but are not limited to: optical sensors for the measurement of transmission through and/or reflection from particulate filters. One class of instruments is differential photometric analyzers, wherein the differences between sequential optical measurements are used to estimate particulate concentrations. System 100 may be the differential photometric analyzer trademarked as the AETHALOMETER® (Magee Scientific Company, Berkeley Calif.) (see for example, U.S. Pat. No. 4,893, 934, incorporated herein by reference); or the Multi Angle Absorption Photometer (see, for example, U.S. Pat. No. 7,038,765), or the Particle Soot Absorption Photometer (see, for example, Bond, T. C., Anderson, T. L., Campbell, D., "Calibration and intercomparison of filter-based measurements of visible light absorption by aerosols," Aerosol Science and Technology, vol. 30, pp 582-600, 1999). System 100 may also be, for example and without limitation, an apparatus that detects electrons transmitted through a filter, as in instruments such as the Beta Attenuation Mass Monitor (see, for example, Macias, E. S.; Husar, R. B., "Atmospheric particulate mass measurement with beta attenuation mass monitor," Environmental Science and Technology, vol. 10, September 1976, p. 904-907); measurements of the vibrational frequency of the filter, as in instruments such as the Tapered Element Oscillating Microbalance (see, for example, Patashnick, H.; Rupprecht, G. "The tapered element oscillating microbalance: A monitor for short-term measurement of fine aerosol mass concentration", Final Report, October 1977- December. Dudley Observatory, Albany, N.Y., 1980.); changes in the electrical properties in volumes 113 and 115, as in instruments such as electrochemical gas analyzers; measurements of radiation from radioactive particulates; or measurements of magnetic properties in the filter.

In one embodiment, the relationship between a useful measure of the constituent of interest and the outputs S1 and S2 may depend on two parameters, such as a linear term and a non-linear term, or a combination of a linear and non-linear function. Given two measurements and two parameters, computer 200 may be then programmed to accept the sensor output and manipulate the sensor output to compute, for example, an estimate of the concentration of the constituent of interest. Examples of such methods are discussed subsequently. Thus system 100 is thus capable of combining two measurements of portions of a flow to provide greater accuracy of a concentration or some characteristic of a constituent of interest. In one embodiment, system 100 may be configured such that each filter 121 and 123 has a different rates of accumulation of constituents of interest (by having different area or flow rates, for example), and provides outputs of sensor 131 or 133 that may be used to provide an improved accuracy by including higher order terms. Several embodiments that utilize different filter loadings are discussed subsequently.

While the embodiment of FIG. 1 illustrates a system 100 that performs two measurements, it is clear to one skilled in the art that other variations are within the scope of the present invention. Thus, for example and without limitation, system 100 may include: a flow-diversion device that accepts a sample and then provides portions of the sample to two separate instruments, where the portions are provided continuously or sequentially to the instruments; or more than two measurements. Further, the analyzers of instrument 110 may be within a housing 101, as in FIG. 1, or alternatively, the analyzers may be in separate housings, and/or some or all of computer 200 or other electronics may reside within housing 101 or separate housings for individual analyzers. In an other alternative embodiment, analyzers, such as analyzers 112 and 114 may share certain components, such as a common light source or a common sensor, that are configured to measure from all flow portions.

FIG. 3 is a schematic of the cross-section of another embodiment of a system 300 and FIG. 4 is a sectional view 4-4 of the embodiment of FIG. 4, and which may be generally similar to system 100, except as further detailed below.

The following discussion refers to system 300 as being an improved AETHALOMETER®. This discussion is for illustrative purpose only, and is not meant to limit the scope of the invention. Specifically, the methods and apparatus described herein are capable of use with other analytical instruments, and, in particular, to all of the analytical instruments and methods described above, in addition to others not mentioned that operate on similar principles.

In one embodiment, system 300 is an improved AETHALOMETER®. The basic AETHALOMETER® has an in-line filter that collects particulates, such as 'Black Carbon' (or "BC') particles, and measures light absorption through the filter over time. Sequential measurements may be used to estimate the density of particles in the sample, as discussed subsequently. The AETHALOMETER® of system 300 includes a fibrous filter tape 320. Tape 320 may be, for example and without limitation, a quartz fiber filter tape that is intended for performing optical transmission measurements for the determination of the presence of particulates. Housing 101 includes an inlet housing 301 and an outlet housing 303 and seals 305 through which tape 320 passes through the housing. Seals 305, which may be O-rings, permit fresh filters to be provided to system 300 without opening the apparatus, with a minimum of down time, and without the exchange of gases between the environment and the apparatus, except through inlet 103 and outlets 105 and 107.

Outlet housing 303 has an opening 322 that forms one side of volume 113 with an area C1 and an opening 324 that forms one side of volume 115 with an area C2. Tape 320 is positioned over openings 322 and 324 so that a portion of the tape is a filter 321 which covers opening 322, and which has a collection area of C1, and a portion of the tape is a filter 323 which covers opening 324, and which has a collection area of C2.

As particulates accumulate on filters 321 and 323, the attenuation of light through the filter increases to the point where accurate measurements are no longer possible. Tape 320 may therefore be replaced or advanced to provide fresh filters 321 and 323. In one embodiment, a mechanism (not shown) may pull the tape to provide fresh filters 321 and 323. In another embodiment, tape 320 is a single-use cartridge that may be replaced manually or by a mechanism (not shown).

In one embodiment, pumps 106 and 108 provide a vacuum to outlets 105 and 107, drawing flow F from the environment and dividing the flow into flow rates F1 and through filters 321 and 323, respectively and holding the tape against output housing 303.

System 300 also includes a light source 330 and photo-detectors 331 and 333. Light source 300 is positioned to illuminate both of filters 321 and 323, and photo-detectors 331 and 333 are configured to detect the transmission of light from the light source through filters 321 and 323, respectively. Photo-detectors 331 and 333 provide outputs S1 and S2, respectively, to computer 200.

In the embodiment of FIG. 3, analyzer 112 includes light source 330, filter 321 and photo-detector 331, and analyzer 114 includes the shared light source, filter 323 and photo-detector 333.

In one embodiment, photo-detectors 331 and 333 produce a single output. Thus, for example, broadband transmission may be detected with a broadband light source 330 and photo-detectors 331 and 333. Alternatively, a monochromatic light source 330, or the placement of an optical filter over a broadband light source, allows photo-detectors 331 and 333 to measure transmission at one wavelength. In another embodiment, measurements are obtained at more than one wavelength, for example N wavelengths $\lambda i$, where $i=1, 2 \ldots N$. Thus, for example, light source 300 may include several emitters, each at a different wavelength. By cycling through the emitters, photo-detectors 331 and 333 may measure the transmission of light at the several wavelengths, resulting in a plurality of signals, such as $S1i$ and $S2i$. The use of a plurality of absorptions measurements in an AETHALOMETER® is described, for example, in Fialho et al. "The Aethalometer calibration and determination of iron concentration in dust aerosols," Journal of Aerosol Science, Volume 37, pages 1497-1506, (2006); or Favez et al. "Ambient measurements of light-absorption by agricultural waste burning organic aerosols," Journal of Aerosol Science, Volume 40, pages 613-620, (2009).

The operation of a single wavelength system 300 will now be discussed. System 300 may be used to measure particulates, such as soot, in the air. With filters 321 and 323 in place and light source 330 turned on, a background reading S10 and S20 is taken of photo-detectors 331 and 333, respectively in the absence of particulates on the filter.

Next pumps 106 and 108 are started, and air at a flow rate F is drawn into inlet 103. The air settles in volume 111 and is eventually drawn into one of the two sampling portions of system 300. Specifically, flow rate F1 is drawn through the area C1 of filter 321 and flow rate F2 is drawn through area C2 of filter 323. Tape 130 may advanced before the filters become saturated with particulates.

In one embodiment, it is advantageous to configure and/or operate system 100 such that the density of the measured constituent of interest on at least two filters (such as filters 321 and 323) occurs at different rates. Thus, for example, in one embodiment of system 100 combinations of flow rates and filter areas are selected such that the density of particulate accumulation on filters (such as filters 321 and 323) occurs at different rates, that is, the mass of particles per time and per unit filter surface area is different for the two filters). It has been found that when this condition is met, it is possible to correct for the effect of filter loading, as discussed subsequently, which tends to result in non-linearities in the calculation of particulate concentration in the air. With reference to system 100 or 300, the rate at which the density of particles collected and accumulated from the flow stream on the filter is proportional to the concentration of particles in the air sample, the flow rate through the filter, and the collecting area of the filter.

As one illustration of systems and/or methods having different densities of measured constituent of interest on at least two filters, which is not meant to limit the scope of the present invention, consider measurements on a sample of air having a concentration, B, of optically-absorbing BC particles that may be accumulated on a filter (such as filters 321 and 323). Further consider the air being drawn through a system 300, and specifically through a pair of in-line filters having an area C1, C2, at a volumetric flow rate F1, F2, respectively. The mass of BC flowing through and caught by the filter per unit time is thus the product of B and the corresponding F, and the density of particles passing through the filter per unit time and area is B F1/C1 and B F2/C2 for the two filters. Given these definitions, differences in accumulation density on the filters, as provided by certain embodiments, can be achieved in a number of ways including, but not limited to the following:

(a) controlling the air flow through outlets 105 and 107 at different flow rates F1 and F2, while the areas C1 and C2 of filters 321 and 323 are approximately equal.

(b) controlling the air flow through outlets 105 and 107 at approximately identical flow rates F1 and F2, while the areas C1 and C2 of filters 321 and 323 are different.

(c) controlling the air flow through outlets 105 and 107 with additional external switching valves such that the flow streams may be switched on and off in rapid succession, with the result that the total flow passing through the filtration collection area during the analytical period may be varied by controlling the on-off ratio of the switching valves. In this variant, the areas C1 and C2 of through filters 321 and 323 may be either identical or different; and the flow rates F1 and F2 (measured when the flow is active) may be either identical or different.

These embodiments essentially replicate the operation of two separate analytical instruments by providing two sample accumulation areas operating at different accumulation rates. Such apparatus could operate with one light source and two photo-detectors to measure the accumulation of particulates on two filters.

As a further example, which is not meant to limit the scope of the present invention, the following is an illustrative, simple method of using an AETHALOMETER®. In certain circumstances, the increase of BC on any one filter is sensed by changes in the transmission of light through that filter. One measure of the decreased transmission of light is referred to as attenuation (or "ATN") according to the following equation: $ATN=100 \ln(S0/S)$, where ln is the natural logarithm, S0 is a background measurement of the intensity of light transmitted through a clean filter, and S is the intensity of light transmitted through the filter when particle-laden. For some instruments, it may be assumed, though not necessary, that the particulate concentration, B, in the sample, is related through the following linear relationship between B and temporally sequential measurements of S in each analyzer 112, 114:

$$B = D \Delta ATN/F \qquad (1)$$

where D is a calibration coefficient, $\Delta ATN$ is the change in ATN between sequential measurements as measured through a filter, and F is the flow rate of the particulate containing sample through the filter. Equation (1) is generally accepted to hold and may be calibrated to give B for a variety of particulates. Specifically for low values of ATN, the simple linear relationship of Equation (1) holds.

However, some detailed measurements have recently found that as ATN increases (that is, as the particulate loading of a filter increases) the linear relationship may no longer hold and, in addition, the amount by which Equation (1) does not hold may vary depending on the conditions that generated the particulate. Thus air pollution particulates generated at one location may have different non-linear effects than particulates generated in a different location.

To correct for variations in the calibration, several embodiments presented herein utilize methods based the postulate that as ATN increases, a non-linear relationship for B holds, generally, $B \propto \Delta ATN/F\, fn(ATN)$, where $fn(ATN)$ is a function of ATN. Further, the methods use multiple measurements, such as from photo-detectors 331 and 333 to deduce the "true" value of B. If $fn(ATN)$ has one parameter, then two measurements of ATN for two portions of the sample may be used to deduce B. For embodiments (a) and (b) above, this calculation requires that the apparatus includes either two flow sensors or other means to accurately know the flow proportioning between the two collection areas. For embodiment (c) above, the method requires that the apparatus has one flow sensor; switching valves; and knowledge of the on-off timing of the flow controlling valves.

As shown subsequently, if system 100 is so operated then it is possible to improve the ability of the apparatus to measure the particulate concentration in the sampled air. It is also possible to measure and report the degree by which the simpler, linear calibration of Equation (1) is in error, thus providing an additional measurement of the particulates. The following derivation is meant to illustrate one embodiment of operating system 300, and is not meant to limit the scope of the present invention.

Consider, for example, a sample of air having a concentration, B, of optically-absorbing BC particles. The value B may be considered to be the "true" particle concentration. The system may be calibrated to provide a linear estimate of the true value of B as B (linear), as follows:

$$B(\text{linear}) = \alpha\, \Delta ATNj/(Fj\, \Delta t), \qquad (2)$$

where $\Delta ATNj$ is the difference between sequential ATN measurements as measured through a filter j, $\Delta t$ is the time between the measurements. and Fj is the volumetric flow rate through the filter. Equation (2) has been found to be generally useful for low values of filter loading (small ATN).

As described subsequently in the Example, there may be a departure from linearity which, for the purpose of this discussion may be represented by:

$$B(\text{non-linear}) = B\{1 - k^* ATNj\}, \qquad (2)$$

where B (non-linear) is the apparatus-dependent nonlinear estimate of the true value of B, and k is the nonlinearity, or 'compensation parameter' that represents the degree of non-linearity. In the absence of non-linearity, k=0 and the instrument response is uniform: there is no change in instrument response between a fresh filter with zero loading, or a heavily-loaded filter just before the system 300 advances tape 320.

In one embodiment, consider the combination of measurements from two independently-operating identical instruments. Further, assume that the two measurements give ATN1 and ATN2, and that these measurements yield estimates denoted B1 and B2 which are believed to deviate by non-linearity from the "true" value B. These measurements may be combined to give a single improved estimate of B, denoted B0, by combining the two parallel measurements values of Equation 3:

$$B1 = B0\{1 - k*ATN1\}, \text{ and} \quad (3a)$$

$$B2 = B0\{1 - k*ATN2\}, \quad (3b)$$

which may be arranged as follows:

$$B0 = \{B1\ ATN2 - B2\ ATN1\}/\{ATN2 - ATN1\}, \text{ and} \quad (4)$$

$$k = \{B1 - B2\}/\{B1\ ATN2 - B2\ ATN1\} \quad (5)$$

Equations 4 and 5 thus permit an improved estimate of the value of B; and the degree to which the apparatus is non-linear by comparing data of two separate instruments operating under analytical conditions that are identical except for having different material loadings. In the absence of non-linearity, k=0 and two ideal instruments would give identical results: B1=B2=B at all values of ATN1 and ATN2. In practice, the comparison of data from two instruments in this manner will always yield the "zero loading" corrected result B0, an improved estimate of the "true" value B. In addition, the method yields a value for the non-linearity parameter k that may provide additional information or insight into the nature, composition or properties of the analyte.

The form of Equations 4 and 5 depend on the form on the non-linearity of Equation 3. Thus, for example, if Equation 3 were an exponential function or another function with one parameter, then different equations would give B0 and k. Alternatively, more than two measurements could be used to provide a least squares estimate of B0 and k, or could be used to fit additional non-linear parameters. All of these embodiments are within the scope of the present invention.

Using system 300, signals from the photo-detectors 331 and 333 yield ATN1 and ATN2, respectively, and their changes from one measurement instant to the next provides the increment from which the concentration data B1 and B2 are calculated using the flow rates F1 and F2, from Equation 2. One single sampling head, comprising two sampling channels operating at different rates of accumulation, thus provides the fundamental data from which the extrapolation back to "zero loading" can be made to eliminate the effects of non-linearity in the analysis.

As an example of another method of deducing the effects on nonlinearly, note that ATN1, ATN2, F1 and F2 are related through: ATN2/F2=ATN1/F1, and F1+F2=F, and thus Equations 3 and 4 we find the following algebraic identities:

$$B0 = (\alpha/F)\{(ATN2+ATN1)/(ATN2-ATN1)\}\{ATN2\ \Delta ATN1/ATN1 - ATN1\ \Delta ATN2/ATN2\} \quad (6)$$

for the "zero loading" result compensated for any non-linearity; and $$k = \{ATN2\ \Delta ATN1 - ATN1\ \Delta ATN2\}/\{ATN2^2\ \Delta ATN1 - ATN1^2\ \Delta ATN2\} \quad (7)$$

for the non-linearity parameter.

Thus the non-linear response may be deduced from the following quantities: ATN1, the optical attenuation due to the accumulated deposit in area 1; ATN2, the optical attenuation due to the accumulated deposit in area 2; $\Delta$ATN1, the change in ATN1 from one measurement to the next; $\Delta$ATN2, the change in ATN2 from one measurement to the next; F, the combined total sample flow rate; and $\alpha$, the parameter that converts the change in A to a mass result B.

The above derivations illustrate that non-linear effects may be accounted for using multiple measurements. Further, these, or other equations may programmed into computer 200, which may then display or transmit estimates of B0 and/or k from the multiple sensors of system 100.

It has been found that in certain situations with specific combinations of location, season, particle composition and optical properties, the non-linearity can be large and the k value is not zero. To improve the performance of any instrument whose measurement principle is based on the determination of an increment, it is advantageous to be able to adapt automatically to situations of perfect linearity, versus serious non-linearity, without requiring any a-priori knowledge of conditions. A fixed correction cannot be applied, because one value may be required for one location, and another (or zero) value required for a different location.

In addition, the compensation parameter k is indicative of the particles being measured. In addition to being able to correct for non-linearities and report a value of B, another embodiment calculates and presents the compensation parameter k, which is a property of the particles being measured. It has been experimentally determined, for example, that the value of k at 880 nm differs strongly for 'fresh' versus 'old' pollution; and that the value of k deduced from measurements taken at an optical wavelength of 880 nm differs from that deduced from measurements taken at an optical wavelength of 370 nm. The value of k thus provides an indication of the history of the particles, and likely also contains information regarding the source of the particles.

In certain embodiments, photo-detectors 331 and 333 measure ATN at a plurality of wavelengths, $\lambda$, which may be written as ATN($\lambda$i), where i=1, 2, . . . , N. These N measurements may then be combined to determine a non-linear response. Thus, for example, values of B0 may be determined for each of the N wavelengths and averages to calculate a value to be reported. In addition, a plurality of k values (ki) may also be calculated and reported as a property of the particulates.

In the embodiments of the methods described above, the nature, magnitude, origin or other attribute of the non-linearity of the analysis; including whether it exists or not; are not required to be known in advance. The mathematics presented in Equations 1-7 is completely general and functional whether or not the value of the non-linearity parameter k is zero, positive or negative. The analytical technique will function on analyses using the same instrument in different locations or under different conditions where the required linearity compensations may be markedly different. The mathematics adapts itself to the data at hand and does not require any previous knowledge or assumption about any specific characteristic of the analyte. This represents a substantial improvement over other instrumental methods that apply corrections, but using fixed mathematical parameters whose effect may be appropriate in one situation but incorrect in another. An additional benefit of this invention is that it yields a value of the non-linearity parameter that may have meaning or interpretation in terms of the composition or other property of the analyte.

EXAMPLE

Figure 5:
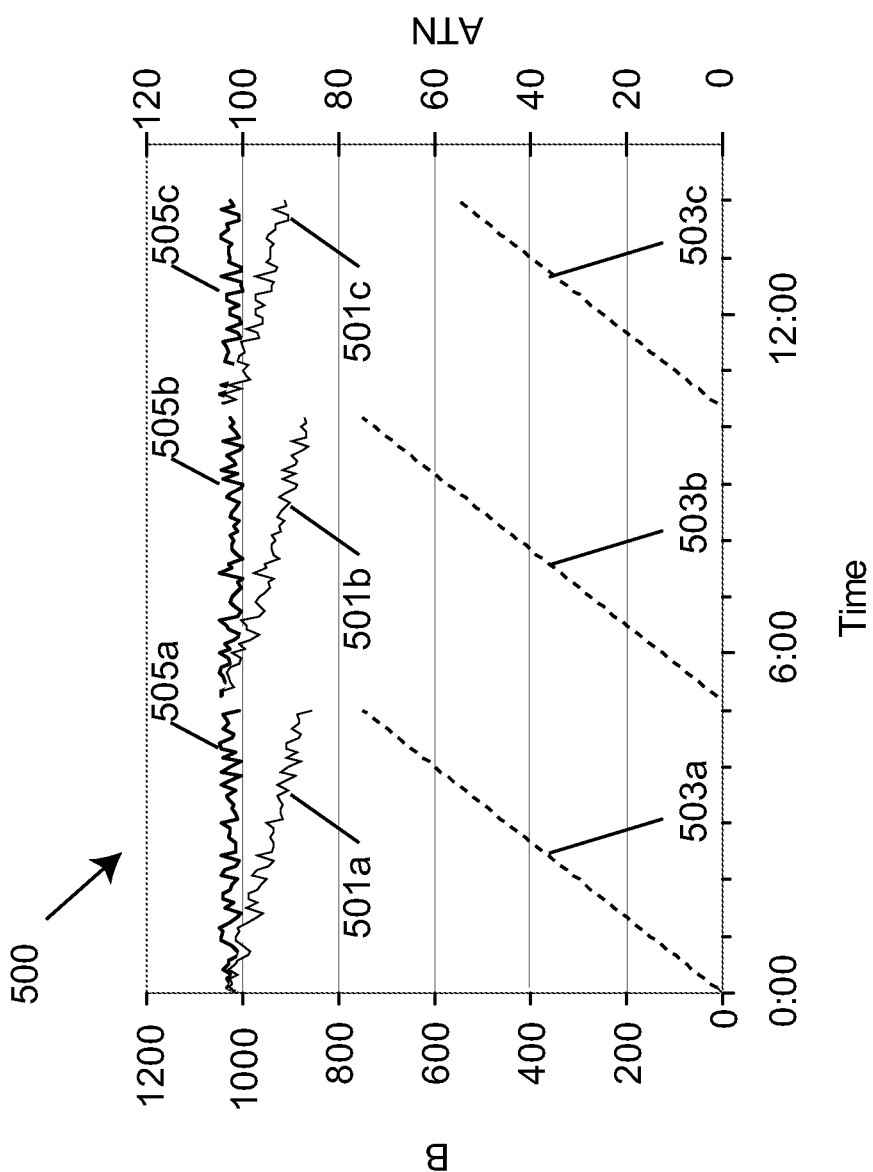
FIG. 5 is graph illustrating an embodiment of a method.

FIG. 5 includes a graph 500 that illustrates the correction of non-linearities at high values of ATN. The data in FIG. 5 were obtained over 15 hours using an Aethalometer model AE-22 in a closed experimental room in which the concentration of BC particles was constant.

Graph 500 shows the results of the AETHALOMETER®, where curves 501a, 501b, and 501c are the estimates of the mass of optically-absorbing 'Black Carbon' material per unit volume of air B using a linear model, the curves 503*a*, 503*b*, and 503*c* are the values of ATN for the filter, and the curves 505*a*, 505*b*, and 505*c* are values of B from curves 501*a*, 501*b*, and 501*c* corrected for nonlinearities. The "a" curves (501*a*, 503*a*, and 505*a*) are from data obtained over the 5 hour interval from 0:00 to 5:00, the "b" curves (501*b*, 503*b*, and 505*b*) are from data obtained over the next 5 hour time interval, from time 5:00 to 10:00, and the "c" curves (501*c*, 503*c*, and 505*c*) are from data obtained over the next 5 hour interval from time 10:00 to 15:00.

The AETHALOMETER® was operated such that when the filter loading reached a pre-set limit, the filter tape would advance to a clean spot and the response would revert to the "BC=0" point of this chart. The tape was changed at the beginning (0:00) and at 5:00 and 10:00. Thus each set of data (a, b, and c) represent the use of the filter, from clean to a pre-set loading limit.

As seen by curves 501*a*, 50 1*b*, and 501*c*, a linear assumption results in irregular behavior. The value of B appears to start out high and then decrease for each new filter. There is a discontinuity in the data at the changing of each filter.

The curves 503*a*, 503*b*, and 503*c* show the total accumulation of ATN on the filter spot, growing from zero (clean filter spot) to a maximum of 75 instrumental units before the loading threshold is reached and the tape advances to a clean spot.

The curves 505*a*, 505*b*, and 505*c* are values of B from curves 501*a*, 501*b*, and 501*c* corrected using the ATN values of 503*a*, 503*b*, and 503*c* using Equation 3. It is seen that the corrected values display no discontinuity between changes of the filter at 5:00 and 10:00. This illustrates that non-linearities due to variations in ATN may be correct, providing for a large improvement in accuracy.

Embodiments have been described using the example of the optical analysis of suspended particles for 'Black Carbon' content as performed by the AETHALOMETER®. It will be understood by those in the art that this method is applicable to a wide range of analytical instruments whose analysis is based on determining the rate of change of an accumulation.

I claim:

1. An apparatus to measure constituents of interest in a sample, said apparatus comprising:
   a first analyzer including a first filter having a first area that accumulates constituents of interest in a first portion of the sample having a first flow rate, and a first detector to measure a property of accumulated constituents of interest on the first filter;
   a second analyzer including a second filter having a second area that accumulates constituents of interest in a second portion of the sample having a second flow rate, and a second detector to measure a property of accumulated constituents of interest on the second filter; and
   a computer to accept the first detector and second detector measurements and provide an indication of the constituents of interest in the flow,
   where said sample, said first portion of the sample, and said second portion of said sample each have a same composition of the constituents of interest.

2. The apparatus of claim 1, wherein said property is an absorption of light at two or more wavelengths through said first filter or second filter.

3. The apparatus of claim 1, where, when accumulating constituents of interest, said first filter and said second filter have different rates of accumulation per filter area.

4. The apparatus of claim 1, where said constituents of interest include carbon black.

5. The apparatus of claim 1, wherein said first analyzer and said second analyzer are differential photometric analyzers.

6. The apparatus of claim 1, further comprising a portion to accept the sample and divide said sample into said first portion and said second portion.

7. The apparatus of claim 1, wherein said first flow rate is different than said second flow rate and where said first area is approximately the same as said second area.

8. The apparatus of claim 1, wherein said first flow rate is approximately equal to said second flow rate and where said first area is different than said second area.

9. The apparatus of claim 1, where said indication is an estimate of the concentration of constituents of interest in the sample.

10. The apparatus of claim 9, where said indication is an indication of a nonlinearity of a response of one or more of said first analyzer and said second analyzer to the estimate of the concentration.

11. An apparatus to measure constituents of interest in a sample, said apparatus comprising:
    a first analyzer including a first filter having a first area to accumulate constituents of interest in a first portion of the sample having a first flow rate, and a first detector to measure a property of accumulated constituents of interest on the first filter;
    a second analyzer including a second filter having a second area to accumulate constituents of interest in a second portion of the sample having a second flow rate, and a second detector to measure a property of accumulated constituents of interest on the second filter; and
    a computer to accept the first detector and second detector measurements and provide an indication of the constituents of interest in the flow,
    wherein said first flow rate is different than said second flow rate and where said first area is approximately the same as said second area.

12. An apparatus to measure constituents of interest in a sample, said apparatus comprising:
    a first analyzer including a first filter having a first area to accumulate constituents of interest in a first portion of the sample having a first flow rate, and a first detector to measure a property of accumulated constituents of interest on the first filter;
    a second analyzer including a second filter having a second area to accumulate constituents of interest in a second portion of the sample having a second flow rate, and a second detector to measure a property of accumulated constituents of interest on the second filter; and
    a computer to accept the first detector and second detector measurements and provide an indication of the constituents of interest in the flow,
    wherein said first flow rate is approximately equal to said second flow rate and where said first area is different than said second area.

13. An apparatus to measure constituents of interest in a sample having two or more sample portions, said apparatus comprising:
    two or more analyzers each including
      a filter that accumulates constituents of interest in a portion of the sample, and
      a detector to measure a property of accumulated constituents of interest; and
      a computer to accept the detectors' measurements and provide an indication of the constituents of interest in the sample,
      where said sample and said two or more sample portions of said sample each have a same composition of the constituents of interest.

14. The apparatus of claim 13, where said indication is an estimate of the concentration of constituents of interest in the sample.

15. The apparatus of claim 13, where said indication is an indication of a nonlinearity of a response of one or more of said two or more analyzers to an estimate of the concentration of constituents of interest in the sample.

16. The apparatus of claim 13, wherein said property is an absorption of light at two or more wavelengths through said filter.

17. The apparatus of claim 13, where said two or more analyzers are two analyzers.

18. The apparatus of claim 13, where said constituents of interest include carbon black.

19. The apparatus of claim 13, wherein said two or more analyzers are differential photometric analyzers.

20. The apparatus of claim 13, further comprising a portion to accept the sample and divide said sample into said two or more sample portions.

21. The apparatus of claim 13,
wherein said two or more analyzers is a first analyzer and a second analyzer,
where said first analyzer provides an indication of particulates accumulated on a first filter having a first area and accumulated from a first portion of the sample having a first flow rate,
where said second analyzer provides an indication of particulates accumulated on a second filter having a second area and accumulated from a second portion of the sample having a second flow rate.

22. The apparatus of claim 21, where, when accumulating constituents of interest, said first filter and said second filter have different rates of accumulation per filter area.

23. The apparatus of claim 21, wherein said first flow rate is different than said second flow rate and where said first area is approximately the same as said second area.

24. The apparatus of claim 21, wherein said first flow rate is approximately equal to said second flow rate and where said first area is different than said second area.

25. An apparatus to measure constituents of interest in a sample having two or more sample portions, said apparatus comprising:
two or more analyzers each including
a filter to accumulate constituents of interest in a portion of the sample, and
a detector to measure a property of accumulated constituents of interest; and
a computer to accept the detector measurements and provide an indication of the constituents of interest in the sample,
wherein said two or more analyzers is a first analyzer and a second analyzer,
where said first analyzer provides an indication of particulates accumulated on a filter having a first area and accumulated from a first portion of the sample having a first flow rate,
where said second analyzer provides an indication of particulates accumulated on a filter having a second area and accumulated from a second portion of the sample having a second flow rate, and
wherein said first flow rate is different than said second flow rate and where said first area is approximately the same as said second area.

26. An apparatus to measure constituents of interest in a sample having two or more sample portions, said apparatus comprising:
two or more analyzers each including
a filter to accumulate constituents of interest in a portion of the sample, and
a detector to measure a property of accumulated constituents of interest; and
a computer to accept the detectors' measurements and provide an indication of the constituents of interest in the sample,
wherein said two or more analyzers is a first analyzer and a second analyzer,
where said first analyzer provides an indication of particulates accumulated on a filter having a first area and accumulated from a first portion of the sample having a first flow rate,
where said second analyzer provides an indication of particulates accumulated on a filter having a second area and accumulated from a second portion of the sample having a second flow rate, andwherein said first flow rate is approximately equal to said second flow rate and where said first area is different than said second area. are differential photometric analyzers.

27. A method for measuring a constituent of interest in a sample having a plurality of samples, said method comprising:
dividing said sample into said plurality of samples each of said plurality of samples having a same composition of the constituent of interest as said sample;
accepting outputs from a plurality of analyzers each adapted to measure the constituent of interest from a corresponding sample of the plurality of samples;
utilizing the outputs from the plurality of analyzers to provide an indication of the constituent of interest in the sample having the plurality of samples.

28. The method of claim 27, wherein said indication is an estimate of the concentration of the constituent of interest in the sample having the plurality of samples.

29. The method of claim 27, wherein said indication is an estimate of a nonlinearity of a response of one or more of said plurality of analyzers to an estimate of the concentration of constituents of interest in the sample having the plurality of samples.

30. The method of claim 27, where said plurality of analyzers measure an absorption of light through a filter positioned to accumulate constituents of interest in the corresponding sample of the plurality of samples.

31. The method of claim 27, where said constituent of interest includes carbon black.

32. The method of claim 27, wherein said plurality of analyzers are differential photometric analyzers.

33. The method of claim 27, where said plurality of analyzers measures a constituent of interest accumulated on a corresponding filter at a rate of accumulation per filter area, and where the values of at least two of said rates of accumulation differ from each other.

* * * * *